United States Patent [19]
Rinn et al.

[11] Patent Number: 5,567,451
[45] Date of Patent: * Oct. 22, 1996

[54] ALGINATE OR PECTATE GEL DEFICIENT IN GELLING IONS FOR USE IN BINDING METAL IONS

[75] Inventors: Jean-Charles Rinn, Cognac; Bertrand Robillard, Epernay, both of France

[73] Assignee: Champagne Moet & Chandon, Epernay, France

[ * ] Notice: The term of this patent shall not extend beyond the expiration date of Pat. No. 5,385,741.

[21] Appl. No.: 368,446

[22] Filed: Jan. 4, 1995

Related U.S. Application Data

[63] Continuation of Ser. No. 940,856, Oct. 23, 1992, Pat. No. 5,385,741.

[30] Foreign Application Priority Data

Feb. 25, 1991 [FR] France .................. 91 02220

[51] Int. Cl.⁶ .................. C12G 1/06; C02F 1/42; C12N 11/10
[52] U.S. Cl. .................. 426/13; 210/681; 210/687; 210/688; 426/15; 435/178; 435/179; 530/412; 530/415
[58] Field of Search .................. 435/178, 179, 435/182; 426/13, 15; 530/412, 415, 417; 210/681, 687, 688

[56] References Cited

U.S. PATENT DOCUMENTS

| | | | |
|---|---|---|---|
| 4,352,883 | 10/1992 | Lim | 435/182 X |
| 4,368,322 | 1/1983 | Muzzarelli | 536/17.2 X |
| 4,663,286 | 5/1987 | Tsang et al. | 435/178 |
| 5,055,402 | 10/1991 | Greens et al. | 435/175 |
| 5,070,019 | 12/1991 | Hill | 435/178 |

FOREIGN PATENT DOCUMENTS

| | | |
|---|---|---|
| 2633937 | 7/1988 | France . |
| 013020 | 2/1981 | Japan . |
| 2119734 | 3/1980 | United Kingdom . |
| 2153780 | 8/1985 | United Kingdom . |
| 2192171 | 1/1988 | United Kingdom . |

OTHER PUBLICATIONS

Veliky, et al., Biotechnology Letters, vol. 1, No. 6, 1981, pp. 275–280.
Amerine, et al., The Technology of Wine Making, 2nd ed., Avi Publ. Co., Westpoint, Conn. 1967 (pp. 296–279, 339 & 340).

*Primary Examiner*—David M. Naff
*Attorney, Agent, or Firm*—Lowe, Price, LeBlanc & Becker

[57] ABSTRACT

An ionically gellable material is gelled with a metal cation and the metal cation content of the gel is reduced to provide the gel with binding sites not occupied by the metal cation so the gel can be used to bind and remove metal cations from solution. In a preferred embodiment, a calcium alginate or calcium pectate gel in the form of beads is prepared, the calcium ion content of the gel is reduced to between 0.01 mg/g and 1.5 mg/g of moist gel by contacting the gel with an aqueous solution of acid such as lactic or tartaric acid having a pH of 1 to 3.5. The gel can be produced containing a microorganism such as yeast used for fermentation so metal ions can be removed while fermenting with the microorganism. In the bottle fermentation of wine to produce champagne, the gel containing yeast is added to the wine in the bottle. During fermentation, calcium and potassium ions are bound by the gel to reduce the precipitation of calcium tartrate and/or potassium bitartrate. Other uses of the gel include binding metal ions which can be other than calcium ions to provide metal ions for regulating enzymic activity or for recognizing, binding or purifying organic materials such as proteins or amino acids.

60 Claims, No Drawings

ALGINATE OR PECTATE GEL DEFICIENT IN GELLING IONS FOR USE IN BINDING METAL IONS

This application is a continuation of application Ser. No. 07/940,856 filed Oct. 23, 1992, now U.S. Pat. No. 5,385,741.

The present invention relates essentially to an ionotropic gel deficient in ionic gelling entity, to a method of preparing such a gel and to a use thereof, especially in a process for the production of sparkling wine such as champagne.

It is known that a category of gels are formed through the binding of ions at certain precise sites on macromolecular chains, called binding sites or cross-linking sites, thus forming bridges between these chains. These ions, which can be designated by the general expression "ionic gelling entity" are for example polyvalent cations, generally divalent or trivalent cations such as the calcium ion or the aluminum ion. The gels formed in this way are sometimes called "ionotropic gels". Alginates, pectates, carrageenans, carboxymethyl cellulose and chitosans may be mentioned among these gels. These gels have been described in particular by J. Klein et al. in Angew. Makromol. Chem. (1979), vol. 76/77, no. 1141, p. 329–50, by K. D. Vorlop et al. in Biotechnol. Lett. (1981), vol. 3, no. 1, p. 9–14, by H. J. Purz et al. in Acta Polymerica (1985), vol. 36, no. 10, p. 569–574, and by R. Berger et al. in Acta Biotechnol. (1988), vol. 8, no. 5, p. 401–405.

Alginic acid and pectic acid, for example, consist of polysaccharide chains and are widespread in the plant kingdom.

Their industrial use is well known, in particular in the food industry and especially for effecting biotransformations.

In the case of alginic acid, for example, polyvalent cations such as the calcium ion, $Ca^{2+}$, form bridges at certain precise sites on the polysaccharide chains, corresponding to polyguluronic sequences, thereby creating a mesh-like structure. This type of crosslinked structure is utilized for example in the immobilization of microorganisms such as bacteria or yeasts, or macromolecules such as enzymes.

Thus, for certain fermentation processes used in the food industries for example, the value of using microorganisms or enzymes not in the free state, but immobilized in appropriate inclusion materials, has been discovered. By virtue of their network-like structure, these materials retain the microorganisms or the enzymes, but remain permeable to the substrates and the fermentation products. Among the principal advantages of this technique, there may be mentioned the fact that it facilitates continuous operation and that it is easier to separate the enzyme systems from the reaction medium (see French patent application A-2 320 349 to INRA, the inclusion material being a polyacrylamide matrix; French patent application A-2 432 045 to INRA, the inclusion material being a polyacrylamide or an alginate (claim 4); and the article in the journal Pour la Science no. 146, December 1989, pages 20 to 21).

According to one of the techniques for the immobilization of yeasts, the latter are suspended in an aqueous solution of sodium alginate. Droplets are formed from said suspension, for example by means of nozzles of small cross-section, and these droplets are then dropped into a solution of calcium chloride to cause the formation of a gel by ionic cross-linking of the alginate, in the form of gelled spheres of about 2 to 3 mm in diameter, commonly known as "beads". These beads are subsequently rinsed to remove the excess calcium chloride and are then used as such in a fermentation process or are either stored in an appropriate aqueous medium or dried for long-term storage (French patent 2 633 937).

Thus the beads prepared in this way, which constitute fermentation biocatalysts, have a high content of calcium ions, principally forming the ionic crosslinking entity. In general, the term "biocatalyst" is understood as meaning a system which is capable of effecting a biochemical reaction, starting from a substrate, under appropriate conditions.

Furthermore, a very frequent problem, especially in the food industries, for example in the preparation of drinks such as fruit juices, wine and champagne, is that of the precipitation of certain compounds, such as potassium bitartrate or calcium tartrate, in the form of crystals. It has been observed, for example in wine, that the solubility of these crystals is largely dependent on the pH, the percentage of alcohol, the ionic strength and the temperature, but also on the supersaturation of the wine with calcium ions and especially with potassium ions. The risks of calcium tartrate precipitation appear when the calcium ion concentration is greater than about 80 mg/l. Now, in certain wines, such as champagne, this concentration is between about 60 and 110 mg/l. In addition, this crystallization phenomenon is particularly important in certain enological processes such as champagne production. In fact, during the secondary ferment in the bottle, the percentage of alcohol increases and precipitates appear which can subsequently only be removed, with relatively uncertain results, by working of the deposit down on to the cork and then extraction of the sediment-coated cork.

It can be seen that the presence of crystalline deposits is highly detrimental to the quality, especially visual quality, of products such as wine and especially champagne.

In the particular case of champagne, the presence of such crystals is also likely to cause the phenomenon known as gushing, i.e. the sudden expulsion of the liquid out of the bottle when it is opened.

Again, in the case of champagne production by the technique involving yeasts immobilized in beads of calcium alginate gel, calcium tartrate crystals can be adsorbed on to the surface of the beads and join them together to form a "plate" of beads, which presents a problem when these plates are subsequently removed from the bottle.

Finally, the formation of these crystals is all the more troublesome and detrimental because it happens, especially in the case of calcium tartrate precipitation, slowly and with a delay, sometimes even after the product has been packaged for sale.

In champagne production, this crystallization phenomenon tends to be worse because biocatalyst beads containing calcium are used, as is the case of beads consisting of calcium alginate.

In fact, the additional introduction of calcium ions into the medium tends to intensify the calcium tartrate precipitation because a significant proportion of the calcium ions present in these beads is gradually released into the wine under the action of physico-chemical phenomena.

As stated earlier, this technical problem of crystalline deposits is not restricted to wine or champagne production, but also exists in a general way in numerous industrial processes involving liquids. There may be mentioned the case of the fruit juice industry, especially the grape juice industry, where tartrate deposits can be observed.

Tartrate precipitations are also found to increase following the deacidification treatment of wine, which consists in raising the pH by the addition of calcium carbonate.

Attempts have been made to overcome this phenomenon of crystalline deposits, for example by inducing the precipitation of these crystals using a variety of means such as a cold pass (S. FERENCZI et al., Bulletin de l'O.I.V. 1982, no. 613, p. 202) or the addition of seed crystals, or alternatively by delaying this precipitation, for example by the addition of metatartaric acid (J. FARKAS et al., Kvasny Prum. 1982, vol. 28, no. 8, p. 176–182; G. PARONETTO, Vignevini 1978, vol. 5, no. 6–7, p. 23–28).

However, these processes are not really satisfactory. In particular, none of them deals with the problem of calcium tartrate precipitation. For example, metatartaric acid is relatively unstable. It hydrolyzes with time and releases tartaric acid. Its addition to wines would therefore tend ultimately to worsen the problem which it is sought to solve.

Furthermore, the concentration of free calcium cations in certain media such as wine increases with time. In fact, it is known that certain ions like the calcium ion are protected by polymeric substances (such as colloids) and will only be released in the longer term.

It would also be possible to envisage using synthetic cation exchange resins to remove the excess cations, but this method is prohibited in enology by legislation in numerous countries, in particular France. In addition, because this technique is non-selective towards numerous cations, it is likely that a substantial quantity of components responsible for the taste quality would be removed.

Thus the technical problem of the precipitation of crystalline deposits in drinks, especially fermented drinks such as wine or champagne, has not been satisfactorily solved hitherto.

One object of the present invention is therefore to solve the novel technical problem which consists in providing a solution enabling the undesirable ions in a given liquid medium to be at least partially removed.

More particularly, one object of the present invention is to solve said technical problem by providing a solution enabling the ions responsible for the formation of crystalline deposits in drinks, especially fermented drinks such as beer, wine and champagne, to be at least partially removed.

A further object of the present invention is to solve the novel technical problem which consists in providing a solution enabling the introduction of ions responsible for precipitations of crystals to be reduced when carrying out processes which involve the use of biocatalysts consisting of an ionotropic gelled material such as calcium alginate.

A further object of the present invention is to solve the novel technical problem which consists in providing a material, forming especially a fermentation biocatalyst, which can not only be used to eliminate the risks of precipitations of crystalline deposits, but can also be used in enzymic processes having an enzymic activity adapted especially by the presence of enzymic activating anions, as well as in processes for the recognition or purification of organic materials, for example as in the case of the clarification of beer to remove the colloids formed.

The present invention makes it possible for the first time to solve the above-mentioned technical problems in a satisfactory manner which can be used on the industrial scale.

Now, it has been discovered, totally surprisingly, that if ionotropic gels, in particular calcium alginate, are treated in order to reduce the proportion of ionic gelling entity, these gels retain their apparent integrity, in particular their structure and their mechanical properties, and can be used in various industrial applications, especially as fermentation biocatalysts, for example in the form of beads.

Thus, according to a first feature, the present invention relates to a solid ionotropic gel, in particular in the form of beads or bound to an appropriate support such as a grid or filament, formed from a material which can be gelled by means of an ionic gelling entity, wherein said gel is deficient in said ionic gelling entity and has ionic binding sites resulting from the absence of said ionic entity, thereby giving it an affinity for ions which are capable of binding to said gel at said binding sites not occupied by the ionic gelling entity.

Preferably, the proportion of ionic gelling entity in the gel according to the invention is less than 0.75 times, preferably less than 0.5 times and particularly preferably between 0.005 times and 0.05 times the maximum proportion corresponding to saturation in said gel of the binding sites for the ionic gelling entity.

In one embodiment of the invention, the above-mentioned gellable material is capable of flowing and can advantageously be used in the form of drops which are gelled by being brought into contact with an aqueous solution containing the above-mentioned ionic gelling entity.

In one particular embodiment of the invention, the above-mentioned gellable material is selected from the group consisting of: the water-soluble salts of alginic acid and pectic acid, especially the alkali metal salts such as the sodium or potassium salts, or the ammonium salt, a carrageenan, especially in the iota and kappa form, chitosan and carboxymethyl cellulose.

In one particularly advantageous embodiment of the invention, the above-mentioned gellable material is a material which can be gelled by the calcium ion. The ionic gelling entity thus consisting of the calcium ion, to obtain an ionotropic gel which is depleted in calcium ions and has an affinity for cations.

In one preferred embodiment, the gel according to the invention consists of calcium alginate in which the proportion of calcium ions is less than 1.5 mg/g of moist gel, preferably less than 1 mg/g and particularly preferably between 0.01 mg/g and 0.1 mg/g of moist gel.

In another advantageous embodiment of the invention, the above-mentioned gellable material constitutes a material for the inclusion of microorganisms, especially fermentation microorganisms such as yeasts, or macromolecules such as enzymes, so as to obtain a gelled biocatalyst which is deficient in ionic crosslinking entity and has an affinity for ions, in particular calcium ions.

Particularly preferably, said ionically gellable inclusion material is an appropriate material compatible with a fermentation medium, in particular in the field of enology and preferably consisting of wine, for the production of sparkling wines and especially champagne. In this application to wine, in particular to sparkling wine and especially champagne, the proportion of ionic gelling entity is preferably less than or equal to about 0.30 times the maximum proportion corresponding to saturation.

Advantageously, said inclusion material is selected from the group consisting of the alkali metal or ammonium salts of alginic or pectic acid, preferably sodium or potassium alginate.

According to a second feature, the present invention relates to a method of preparing a solid ionotropic gel deficient in ionic gelling entity, comprising the gelling of an ionically gellable material containing binding sites—or crosslinking sites—to which said ionic gelling entity binds, thereby producing, in the gel thus formed, saturation of the binding sites for said ionic entity, wherein, after gelling by said ionic gelling entity, the proportion of ionic gelling entity is brought to a level below that of said saturation.

Advantageously, according to a preferred characteristic of the mode of carrying out the method according to the invention, the proportion of ionic gelling entity is brought to a level which is less than 0.75 times and preferably less than 0.5 times that of the maximum proportion corresponding to the above-mentioned saturation, and particularly preferably between 0.005 times and 0.05 times that of said maximum proportion.

In one particularly advantageous mode of carrying out the method according to the invention, the above-mentioned proportion of ionic entity in the gel formed by the gelling of said ionically gellable material is reduced by ion exchange, in particular with protons, for example by bringing an aqueous solution of an acid into contact with the above-mentioned gel so that ion exchange takes place between said ionic entity and the proton.

The pH of said aqueous solution of acid is preferably between 1 and 3.5 and particularly preferably between 2.5 and 3.2.

The nature of the chosen acid is not really critical. In particular, hydrochloric acid may be used at a concentration corresponding to a suitable pH. In some cases, in particular when the gel according to the invention is to be used in a fermentation process, for example in enology, it will be preferable to choose an acid acceptable in foodstuffs, such as lactic acid. However, it will be advantageous to choose an acid which is capable of forming a complex with the ionic gelling entity, making it possible to accelerate the reduction of the proportion of ionic gelling entity in the treated gel. For example, in particular when the ionic gelling entity is the calcium ion, the acid used will be an organic diacid in which the two acid groups preferably occupy the I and 4 positions, such as tartaric acid.

The particular characteristics described above in relation to the gel according to the invention also apply to the present method of preparation. In particular, the gellable material is advantageously capable of flowing in the form of drops, which are converted to gelled beads by reaction with an aqueous solution containing the ionic gelling entity.

In one particular mode of carrying out the method of preparing the gel according to the invention, said method comprises using, as the ionically gellable material, a material which is compatible with a fermentation medium, in particular in the field of enology and preferably consisting of wine, for the production of sparkling wines and especially champagne.

A preferred ionically gellable material consists of an alkali metal alginate such as sodium or potassium alginate, or ammonium alginate, the ionic crosslinking entity consisting of the calcium ion.

In one particular mode of carrying out the method of the invention, the ionically gellable material consists of a material for the inclusion of microorganisms, especially fermentation microorganisms such as yeasts, or macromolecules such as enzymes, so as to obtain a gelled biocatalyst which is deficient in ionic crosslinking entity and has an affinity for ions, in particular calcium ions.

The quantity of yeast cells, such as Saccharomyces cerevisiae cells, included in the gel is of the same order of magnitude as in the case of the immobilization of yeast cells in known gels; for example, this quantity is between 100 million and 600 million yeast cells per milliliter of gel. If appropriate, it is also possible to use a gel with a double layer structure comprising a core in which the microorganism cells are included, and an outer layer devoid of said cells.

In one embodiment for which the proportion of ionic gelling entity is to be lowered to a relatively small extent, for example to less than about 0.30 times the maximum proportion at saturation, as in the application in enology, the lowering can be effected at a temperature around room temperature, for example at about 20° C.

In one particularly valuable modification of the above-mentioned embodiment, when the proportion of ionic entity is to be very small, the proportion of ionic gelling entity is lowered at a temperature of between 4° C. and 10° C., preferably at about 4° C.

In another preferred modification of the above-mentioned embodiment, during the operation of lowering the proportion of ionic gelling entity, nutrient substrate is introduced into the medium containing the gel or biocatalyst, in a quantity which is just sufficient to ensure the viability of the microorganisms, such as the yeasts, included in said gel or biocatalyst. For example, in the case of Saccharomyces cerevisiae, the quantity of substrate introduced into this medium will be about 0.4 mg of sucrose per hour for $300.10^6$ cells.

According to one advantageous characteristic of the above-mentioned mode of carrying out the method according to the invention, the pH of the above-mentioned acid solution is maintained at a value of at least 2.7 when the gel contains microorganism cells, such as yeast cells, so as to preserve the activity of said cells.

In yet another mode of carrying out the method according to the invention, after the step for depletion of the ionic gelling entity, a further ion exchange can be carried out in order to introduce a metal ion for a particular purpose, such as enzymic activation or the recognition, binding or purification of an organic material such as proteins or amino acids. These metal ions are preferably selected from the group consisting of magnesium, manganese, zinc, potassium, iron, copper, calcium, cobalt and molybdenum.

It will be observed that the invention is particularly valuable in these uses because the initial depletion of the ionic gelling entity makes it possible to obtain a clean reaction medium and to regulate the proportion of the addition of one or other of the above-mentioned metal ions very precisely and extremely reproducibly and reliably. It is thus possible to regulate the enzymic activity since numerous enzymes require the presence of a metal ion for their activity and, by virtue of the invention, this metal ion is present in a very precise quantity and is stable due to inclusion in the gel according to the invention, the metal ion participating in the chemical structure of this gel.

The presence of this metal ion in a very precise and reliable quantity also makes it possible to bind or purify organic materials, in particular proteins or amino acids, because these proteins or these amino acids have sites or groups which bind preferentially to metal ions. An example which may be mentioned is the recognition of histidine by the copper ion or the zinc ion.

According to a third feature, the present invention relates to the use of the gel according to the invention, such as defined above, as a material for trapping ions, in particular cations.

In one particular embodiment, the gel according to the invention, in particular in the form of beads, is used in the food industry, especially in the fruit juice industry and in enology, for preventing or reducing the risks of the precipitation of crystals such as potassium bitartrate and calcium tartrate.

In one particular modification of the above-mentioned embodiment, an ionotropic gel, such as calcium alginate, which is deficient in ionic gelling entity, such as defined above, preferably in the form of beads, is used in a "bottle fermentation" process, in particular according to the so-called "champagne method", which consists of the secondary ferment of a wine, such as a champagne wine, after the addition of sugar to give a sparkling wine. Advantageously, the above-mentioned gel contains yeasts such as *Saccharomyces cerevisiae* or *Saccharomyces bayanus*. The concentration of yeasts is preferably between $10^8$ and $6.10^8$ yeast cells per milliliter of gel.

The quantity of yeast-containing gel according to the invention, preferably in the form of beads, which is introduced into each 75 cl bottle for the "bottle fermentation" process is generally about 4 ml for a concentration of about $3.10^8$ yeast cells per milliliter of gel.

The field of the present invention also covers the use, in the above-mentioned "bottle fermentation" process, of "classical" beads of calcium alginate gel, i.e. beads not deficient in calcium ions, including yeasts, to which beads of gel according to the invention which do not incorporate yeast are added, the sole purpose of the latter beads being to trap the undesirable cations such as the potassium ions and the calcium ions.

It will be noted, however, that experience has shown that the use, in the "bottle fermentation" process, of beads of calcium-deficient calcium alginate gel according to the invention, including yeasts, has an important and unexpected advantage in terms of the cloudiness of the sparkling wine obtained. In fact, this cloudiness is greatly reduced in the case where the beads according to the invention are used, compared with the case where the classical beads, which are not deficient in calcium ions, are used. With the beads according to the invention, and in particular those in which the proportion of calcium is less than or equal to about 0.30 times the maximum proportion at saturation, not only are the tartrate precipitations avoided, but also the escape of yeasts out of the beads into the wine is very greatly reduced or even non-existent. This advantage may make it unnecessary to use a gel with a double layer structure, such as defined above, as a biocatalyst.

Furthermore, it will be observed that in order to effect the "bottle fermentation" of the champagne wine by means of the beads according to the invention, it is generally sufficient if the proportion of calcium in these beads is lowered to about 0.60 g/kg of moist beads, corresponding to a proportion of calcium of about 0.30 times the maximum proportion in the gel, in order to avoid any subsequent risk of precipitation of calcium tartrate in the wine.

In another embodiment of the invention, the gel according to the invention, in particular in the form of beads or bound to an appropriate support such as a grid or filament, is used in processes for the removal of heavy metals such as lead, barium, cobalt, iron, manganese and copper. Advantageously, the gel according to the invention can be used, for example as column packing, for the continuous treatment of water, especially the treatment of urban or industrial effluents.

According to a fourth feature, the present invention relates to the use of the gel according to the invention, such as defined above, in an enzymic process, thus making it possible to regulate the enzymic activity, in which case said gel comprises a determined proportion of enzymic activating ion. Such an enzymic activating ion is selected in particular from the group consisting of magnesium, manganese, zinc, potassium, iron, copper, calcium, cobalt and molybdenum.

Finally, according to a fifth feature, the present invention further relates to the use of the gel according to the invention, such as defined above, in a process for the binding or purification of organic materials, in particular proteins or amino acids, or else in a process for the recognition of such proteins or amino acids. Within this framework, the gel of the invention then contains a predetermined quantity of binding metal ions selected from the group listed above, which make it possible to bind the organic material, in particular proteins or amino acids.

Further objects, characteristics and advantages of the invention will become more clearly apparent from the following explanatory description referring to several Examples of the invention, which are given simply by way of illustration and cannot therefore in any way limit the scope of the invention.

EXAMPLE 1

Preparation of the gel according to the invention, deficient in ionic gelling entity A gel in the form of beads is prepared in known manner from a 1.2% by weight solution of sodium alginate obtained by mixing 120 g of sodium alginate with 10 l of distilled water.

Droplets are produced by running the alginate solution dropwise into a gelling bath consisting of an approximately 16% by weight aqueous solution of calcium chloride, said dropwise addition being effected with the aid of a classical drop-forming apparatus which can contain a vertical tube with an internal diameter of about 0.5 mm. When a drop falls into the crosslinking bath, an approximately 3 mm bead of gel is formed, the calcium ion constituting an ionic gelling entity for the sodium alginate, and the latter constituting a material which can be ionically gelled by exchange of the $Na^+$ ions with the $Ca^{2+}$ ions, this technique being well known to those skilled in the art.

These beads formed in this way are agitated gently in the $CaCl_2$ solution for an appropriate time to complete the crosslinking. The beads are then sieved and washed several times with demineralized water.

After four rinses, the calcium concentration in these beads obtained direct from crosslinking is of the order of 2 g/kg of moist beads.

According to the invention, these beads are depleted in ionic gelling entity, in this case calcium, in the following manner:

10 l of previously prepared beads of gel are introduced into a 50 l tank equipped with a mechanical agitator, and an aqueous solution of tartaric acid with a pH of between 2.5 and 3.2, preferably 2.7, corresponding to a concentration by weight of about 0.05% of tartaric acid, is passed through continuously, for example by means of an inlet at the bottom of the tank and an overflow at the top. The volume of acid solution is adjusted to about twice that of the beads, i.e. to about 20 l in this case. The rate of flow of the acid solution through the tank is adjusted to about 100 l/h and its temperature can be room temperature, i.e. between 18° C. and 25° C.

While this solution is passing through, gentle agitation is maintained so as not to damage the beads of gel.

According to the analysis of the samples taken, the proportion of calcium in the beads, which was about 2 g/kg prior to treatment, is seen to fall fairly rapidly to reach about 1 g/kg after 2 h 30 min and about 0.4 g/kg after 5 h.

If this treatment is continued for a longer period of time under the same conditions, the calcium concentration in the beads decreases more slowly: 0.3 g/kg after 10 h, 0.1 g/kg after 18 h and about 0.05 g/kg after 24 h.

It is also observed that the diameter of the beads decreases substantially during the above-mentioned ion exchange. This decrease is about 25% after 24 h for beads measuring about 3 mm prior to treatment.

Finally, it is noted, unexpectedly, that the structure of the gel forming these beads does not seem to have been modified by the process described, apart from the observed contraction effect. In particular, their mechanical properties are preserved, making them suitable in particular for industrial uses such as those described above.

EXAMPLE 2

Preparation of a gel according to the invention, constituting a fermentation biocatalyst Beads of alginate gel are prepared in a first step, as in Example 1, by gelling drops of an aqueous solution of sodium alginate in the presence of an aqueous solution of calcium chloride. In the present case, however, the beads prepared have a so-called "double layer" structure, i.e. a structure formed of a core consisting of calcium alginate gel including cells of the yeast Saccharomyces cerevisiae, surrounded by a layer of the same gel but substantially devoid of yeast cells. This is done using a device such as that described in German patent 3 432 923, FIG. 5, consisting essentially of two vertical coaxial nozzles which are arranged so that the end of the central nozzle is slightly lower than that of the peripheral nozzle, and the dimensions of which are such that they enable two aqueous solutions to flow dropwise simultaneously, one through the central nozzle and the other through the peripheral nozzle, the second solution forming a film around the first. The solution arriving through the central nozzle is a 1.2% by weight aqueous solution of sodium alginate containing about $3 10^{11}$ cells per liter, and the solution arriving through the peripheral nozzle is an aqueous solution of sodium alginate of the same concentration but not containing any cells.

As in Example 1, the drops fall into a gelling bath consisting of an approximately 16% by weight aqueous solution of calcium chloride. This procedure immobilizes the yeasts in the beads of gel thus formed.

In the next step, which consists in reducing the proportion of calcium in the beads, the procedure of Example 1 is followed again except that a 50% aqueous solution of sucrose is additionally fed in at a rate of 80 ml/h. Furthermore, the operating conditions are in particular as follows: the pH of the tartaric acid solution is between 2.7 and 2.9 and its temperature is maintained at 4° C.

In a first modification, the treatment with the acid solution is stopped as soon as the proportion of calcium in the beads reaches about 0.1 g/kg, which, under the above-mentioned operating conditions, corresponds to a treatment time of about 16 to 18 h.

In a second modification permitting an accelerated treatment, when it suffices, for the subsequent use of the biocatalysts according to the invention, for example in the bottle fermentation process, to have a proportion of calcium in the alginate beads of about 0.30 times the maximum proportion at saturation, i.e. about 0.65 g/kg of moist alginate beads, the treatment is carried out with a 1% aqueous solution of tartaric acid at a temperature around room temperature, for example at about 20° C., said treatment then taking only about 1 h 30 min, which is sufficient to preserve the yeasts. Furthermore, it is observed in this case that the yeast activity is not impaired, even if there is no additional feed of aqueous sucrose solution.

EXAMPLE 3

Use of the biocatalyst of Example 2 for effecting the "bottle fermentation" of champagne The beads used are calcium-deficient beads obtained in Example 2, containing Saccharomyces cerevisiae cells and having a titer of 0.1 g of calcium per kilogram of moist beads. 4 ml of these moist beads are introduced into each 750 ml bottle containing wine sweetened at a rate of 24 g/l of sucrose. The bottles are hermetically sealed with a cap and laid horizontally in a cellar so as to allow the fermentation known as "bottle fermentation" to take place.

Samples taken after 13 days of fermentation show that there is a decrease of about 10 mg/l in the proportion of calcium in the wine and a decrease of about 30 mg/l in the proportion of potassium. Furthermore, no formation of crystals is observed in the samples taken.

After six weeks in this position, the bottles are turned upside down to enable the beads, which are denser than the wine, to move down towards the neck, which generally happens in a few seconds. The classical champagne method is then adopted, i.e. the wine situated in the lower part of the neck is frozen by means of a brine so as to trap the beads in a plug of ice; this is then knocked out after the bottle has been uncapped.

Thus, through using this calcium-depleted biomaterial, it has been possible to stabilize the wine in respect of the calcium and/or the potassium, while at the same time effecting an undisturbed alcoholic fermentation. Furthermore, it is observed, unexpectedly, that the wine is less cloudy after the "bottle fermentation", whereas in the case of the known "bottle fermentation" processes, with or without included yeasts, there always remains a very slight cloudiness due partly to the presence of colloids originating from the yeast.

EXAMPLE 4

Use of the biomaterial according to the invention for regulating the enzymic activity or for recognizing, binding or purifying organic materials such as proteins or amino acids The beads of gel prepared in Example 1 are used as the starting material for the preparation of a biomaterial containing a metal ion in a quantity adjusted reproducibly by classical ion exchange. This metal ion can be selected from magnesium, manganese, zinc, potassium, iron, copper, calcium, cobalt, molybdenum or any combination thereof.

For example, an adjusted quantity of copper is introduced by using a 3% aqueous solution of copper sulfate to effect ion exchange between the copper ions and the protons in the gel.

To do this, 100 ml of moist beads prepared in Example 1 are introduced into 200 ml of the copper sulfate solution. The pH of the medium, which was 4.5 prior to the addition of the beads, drops rapidly to 2.7 and then reaches 2.3 after 2 h at room temperature.

This gives a biomaterial of adjusted enzymic activity which can be used in any enzymic process, as is clearly apparent to those skilled in the art.

It is also possible to recognize proteins or amino acids by also using zinc as the metal ion. This makes it possible to recognize histidine, for example, as is also well known to those skilled in the art.

Another application of the invention in the field of enzymic activation consists in a first step in preparing beads of ionotropic gel immobilizing an enzyme corresponding in each case to a different activating cation. Enzyme immobilization processes are well known to those skilled in the art. Reference may be made especially to the work by M. MOO-YOUNG (ed.), "Bioreactor immobilized enzymes and cells: fundamentals and applications", Elsevier Appl. Sci. Publish. (New York) 1988, and in particular to the articles by A. Illanes et al. and by C. Dauner-Schütze et al.

In a second step, the ionic crosslinking entity is at least partially replaced with protons by the method of the present invention.

At the time when such biomaterials are used, it will suffice to replace the protons with the cation corresponding to the enzyme which it is desired to activate.

EXAMPLE 5

Comparative experiments on the treatment of water and wine to remove heavy metals In the present Example, 4 ml of alginate beads deficient in ionic crosslinking entity, prepared in Example 1, are placed in a first column ($C_1$) and 4 ml of untreated calcium alginate beads are placed in a second column ($C_2$). A third column contains no beads and serves as a control column.

250 ml of water or wine are passed through each of these three columns at a rate of 85 ml/h for 4 h. The ion concentration is determined before and after the column treatment. The results are shown in Tables I and II below:

TABLE I

| Concentration | Untreated water | $C_1$: "calcium-depleted" beads | $C_2$: "normal" beads |
| --- | --- | --- | --- |
| Mn | 260 | <2 | 60 |
| Ba | 80 | <1 | <1 |
| Cu | 50 | <5 | <5 |
| Co | 135 | <10 | 30 |

TABLE II

| Concentration (ppm) | Untreated wine | $C_1$: "calcium-depleted" beads | $C_2$: "normal" beads |
| --- | --- | --- | --- |
| Co | 1.24 | 0.98 (−21%) | 1.12 (−10%) |
| Cu | 3.10 | 1.96 (−37%) | 2.62 (−15.5%) |
| Fe | 3.05 | 2.75 (−10%) | 3.00 (−2%) |

It is seen that the treatment with the calcium-depleted beads according to the invention ($C_1$) results in a substantial decrease in the concentration of heavy metals.

It will also be seen that a decrease in the concentration of heavy metals is observed when using so-called normal beads, i.e. beads not depleted in calcium; this is probably due to an absorption effect of the heavy metals on the surface of the beads. Nevertheless, the calcium-depleted beads according to the invention afford an unexpected improvement in the absorption of heavy metals, which is all the more remarkable because it makes it possible to obtain extremely low concentrations of certain heavy metals.

It follows that the gels according to the invention can advantageously be used as a means of reducing the proportion of heavy metals in various liquids. Especially in the agri-foodstuffs sector, it is particularly valuable to be able to treat products contaminated by heavy metals as a result of treatments or environmental pollution.

What is claimed is:

1. A method of preparation of a solid gel selected from the group consisting of an alginate and a pectate gel, said gel being partially deficient in calcium ions, comprising the successive steps of:

(a) preparing a solution of a solubilized form of said gel selected from the group consisting of alginic acid, pectic acid, water-soluble salts of alginic acid, and water-soluble salts of pectic acid, (b) preparing a solution of a calcium salt capable of gelling said solution of said solubilized form of said gel, (c) contacting said solution of said solubilized form of said gel with said calcium salt solution under conditions capable of gelling said solubilized form of said gel as a calcium alginate or pectate gel, wherein said calcium alginate or pectate gel has a calcium ion content corresponding substantially to saturation of the binding sites of the alginate or pectate gel, (d) reducing by ion exchange of calcium ions with protons the content of said calcium ions in the alginate or pectate gel by contacting said gel with an aqueous solution of acid having a pH between 1 and 3.5 during a period of time sufficient to lower the content of said calcium ions in said gel to between about 0.01 mg/g and about 1.5 mg/g of moist alginate or pectate gel, so that said gel is deficient in calcium ions, has ionic binding sites resulting from the absences of said calcium ion and has an affinity for ions capable of binding to said gel at binding sites not occupied by calcium ions, and (e) recovering said calcium alginate or pectate gel partially deficient in cation ions, whereby said gel has an affinity for ions capable of binding to said gel at said binding sites not occupied by calcium ions.

2. The method of claim 1, wherein said step (d) is performed with an aqueous solution of acid having a pH ranging between 2.5 and 3.2.

3. The method of claim 1, wherein said step (d) is performed with an acid acceptable in foodstuff.

4. The method of claim 1, wherein said acid in step (d) is lactic acid.

5. The method of claim 1, wherein said acid in step (d) is capable of forming a complex with calcium, so as to accelerate the reduction of the content of cation ions in the gel.

6. The method of claim 5, wherein said acid is an organic diacid in which the acid groups occupy the one and the four positions.

7. The method of claim 6, wherein said diacid is tartaric acid.

8. The method of claim 1, wherein said solution of solubilized form of said gel contains fermentation microorganisms.

9. The method of claim 8, wherein said fermentation microorganisms are yeasts.

10. The method of claim 8, wherein said alginate or pectate gel is a gel with a double layer structure comprising a core in which fermentation microorganisms are included, and an outer layer devoid of said microorganisms.

11. The method of claim 8, wherein the content of calcium in the gel is lowered while said alginate or pectate gel is at a temperature between 4° C. and 10° C.

12. The method of claim 8, wherein during the reduction of the content of calcium ions, a nutrient substrate is introduced into the medium containing the gel in a quantity just sufficient to ensure the viability of the microorganisms, included in said gel.

13. The method of claim 12, wherein the microorganisms are *Saccharomyces cerevisiae* and the quantity of nutrient substrate introduced into this medium is about 0.4 g of sucrose per hour for 300×10⁹ *Saccharomyces cerevisiae* cells.

14. The method of claim 8, wherein the pH of the acid solution is maintained from 2.7 to 3.5 so as to preserve the activity of said microorganism.

15. The method of claim 1, wherein after reducing the content of calcium ions in the gel, a further metal ion exchange is carried out to introduce a metal cation other than a calcium ion.

16. A method for preventing or reducing the risk of precipitation of crystals including potassium bitartrate and calcium tartrate in a liquid containing ions capable of forming said crystals, said method comprising contacting said liquid with said calcium alginate or pectate gel partially deficient in calcium ions produced by the method of claim 1 whereby said gel binds said ions capable of forming said crystals at binding sites of said gel not occupied by calcium ions; and separating said gel having said bound ions capable of forming said crystals.

17. The method of claim 16, wherein said liquid is selected from the group consisting of fruit juice, wine, sparkling wine, and champagne.

18. The method of claim 16, wherein said gel is used in a bottle fermentation process for the secondary fermentation of a wine after the addition of sugar to give a sparkling wine.

19. The method of claim 18, wherein said gel contains yeasts.

20. The method of claim 19, wherein the concentration of yeasts ranges between $10^8$ and $6 \times 10^8$ yeast cells per milliliter of gel.

21. The method of claim 20, wherein said yeasts are selected from the group consisting of *Saccharomyces cerevisiae* and *Saccharomyces bayanus*.

22. The method of claim 21, wherein the quantity of yeast-containing gel which is introduced is about 4 ml to provide a concentration of about $3 \times 10^8$ yeast cells per milliliter of gel.

23. The method of claim 16, wherein the gel which is partially deficient in calcium ions is used in combination with a calcium alginate gel which is not deficient in calcium ions and includes yeasts.

24. The method of claim 16, wherein said gel is in the form of beads.

25. A solid pectate gel partially deficient in calcium ions formed by a process comprising the successive steps of:

(a) preparing a solution of pectic acid or a water-soluble pectate salt having ionic binding sites for calcium ions, (b) preparing a solution of a calcium salt capable of gelling said solution of said pectic acid or said water-soluble pectate salt, (c) contacting said solution of said pectic acid or said water-soluble pectate salt with said calcium salt solution under conditions capable of gelling said pectic acid or said water-soluble pectate salt as a calcium pectate gel, wherein said calcium pectate gel has a calcium ion content corresponding substantially to saturation of the binding sites of the pectate, (d) reducing by ion exchange of calcium ions with protons the content of said calcium ions in the pectate gel by contacting said gel with an aqueous solution of acid having a pH between 1 and 3.5 during a period of time sufficient to lower the content of said calcium ions in said gel to between about 0.01 mg/g and about 1.5 mg/g of moist pectate gel, so that said gel is deficient in calcium ions, has ionic binding sites resulting from the absences of said calcium ion and has an affinity for ions capable of binding to said gel at binding sites not occupied by calcium ions, and (e) recovering said calcium pectate gel partially deficient in cation ions, whereby said gel has an affinity for ions capable of binding to said gel at said binding sites not occupied by calcium ions.

26. The gel of claim 25, wherein said step (d) is performed with an aqueous solution of acid having a pH ranging between 2.5 and 3.2.

27. The gel of claim 25, wherein said step (d) is performed with an acid acceptable in foodstuff.

28. The gel of claim 25, wherein said acid in step (d) is lactic acid.

29. The gel of claim 25, wherein said acid in step (d) is capable of forming a complex with calcium, so as to accelerate the reduction of the content of calcium ions in the gel.

30. The gel of claim 29, wherein said acid is an organic diacid in which the acid groups occupied the one and the four positions.

31. The gel of claim 30, wherein said diacid is tartaric acid.

32. The gel of claim 25, wherein said solution of pectic acid or water-soluble pectate salt contains fermentation microorganisms.

33. The gel of claim 32, wherein said fermentation microorganisms are yeasts.

34. The gel of claim 32, wherein said pectate gel is a gel with a double layer structure comprising a core in which fermentation microorganisms are included, and an outer layer devoid of said microorganisms.

35. The gel of claim 25, wherein the content of calcium in the gel is lowered while said pectate gel is at a temperature between 4° C. and 10° C.

36. The gel of claim 32, wherein during the reduction of the content of calcium ions, a nutrient substrate is introduced into the medium containing the gel in a quality just sufficient to ensure the viability of the microorganisms, included in said gel.

37. The gel of claim 32, wherein the microorganisms are *Saccharomyces cerevisiae* and the quantity of nutrient substrate introduced into this medium is about 0.4 g of sucrose per hour for $300 \times 10^9$ *Saccharomyces cerevisiae* cells.

38. The gel of claim 32, wherein the pH of the acid solution is maintained from 2.7 to 3.5 so as to preserve the activity of said microorganism.

39. The gel of claim 25, wherein after reducing the content of calcium ions in the gel, a further metal ion exchange is carried out to introduce a metal cation other than a calcium ion.

40. A solid alginate or pectate gel partially deficient in ionic gelling entity formed by a process comprising the successive steps of:

(a) preparing a solution of a solubilized form of said gel selected from the group consisting of alginic acid, pectic acid, water-soluble salts of alginic acid, and water-soluble salts of pectic acid, (b) preparing a solution of an ionic gelling entity capable of gelling said solution of said solubilized form of said gel, (c) contacting said solution of said solubilized form of said gel with said solution of said ionic gelling entity under conditions capable of gelling said solubilized form of said gel as an alginate or pectate gel, wherein said alginate or pectate gel has an ionic gelling entity content corresponding essentially to saturation of the binding sites of the alginate or pectate gel, (d) reducing by ion exchange of the ions of said gelling entity with protons, the content of said ion gelling entity in the alginate or pectate gel by contacting said gel with an aqueous solution of acid having a pH between 1 and 3.5 during a period of time sufficient to lower the content of said ion gelling entity in said gel to between 0.005 times and 0.75 times said content of ion gelling entity corresponding essentially to saturation of the binding sites of the alginate or pectate gel, so that said gel is deficient in ion gelling entity, as ionic binding sites resulting from the absences of said ion gelling entity and has an affinity for ions capable of binding to said gel at binding sites not occupied by said ion gelling entity, and (e) recovering said alginate or pectate gel partially deficient in ionic gelling entity, whereby said gel has an affinity for ions capable of binding to said gel at said binding sites not occupied by said ionic gelling entity.

41. The gel of claim 40, wherein said ionic gelling entity is calcium ions.

42. The gel of claim 40, wherein said water-soluble salts of alginic acid and pectic acid are alkali metal salts.

43. The gel of claim 42, wherein said alkali metal salts are selected from the group consisting of sodium, potassium and ammonium.

44. The gel of claim 40, wherein said step (d) is performed at said pH during a period of time sufficient to lower the content of said ionic gelling entity in the gel between 0.005 times and 0.5 times the ionic gelling entity content corresponding essentially to saturation of the binding sites of the alginate or pectate gel.

45. The gel of claim 40, wherein said step (d) is performed at said pH during a period of time sufficient to lower the content of said ionic gelling entity between 0.005 times and 0.05 times the ionic gelling entity content corresponding essentially to saturation of the binding sites of the alginate or pectate gel.

46. A method of preparation of a solid gel selected from the group consisting of an alginate and a pectate gel, said gel being partially deficient in an ionic gelling entity, comprising the successive steps of:

(a) preparing a solution of a solubilized form of said gel selected from the group consisting of alginic acid, pectic acid, water-soluble salts of alginic acid, and water-soluble salts of pectic acid, (b) preparing a solution of an ionic gelling entity capable of gelling said solution of said solubilized form of said gel, (c) contacting said solution of said solubilized form of said gel with said solution of said ionic gelling entity under conditions capable of gelling said solubilized form of said gel as an alginate or pectate gel, wherein said alginate or pectate gel has an ionic gelling entity content corresponding essentially to saturation of the binding sites of the alginate or pectate gel, (d) reducing by ion exchange of the ions of said gelling entity with protons, the content of said ion gelling entity in the alginate or pectate gel by contacting said gel with an aqueous solution of acid having a pH between 1 and 3.5 during a period of time sufficient to lower the content of said ion gelling entity in said gel to between 0.005 times and 0.75 times said content of ion gelling entity corresponding essentially to saturation of the binding sites of the alginate or pectate gel, so that said gel is deficient in ion gelling entity, as ionic binding sites resulting from the absences of said ion gelling entity and has an affinity for ions capable of binding to said gel at binding sites not occupied by said ion gelling entity, and (e) recovering said alginate or pectate gel partially deficient in ionic gelling entity, whereby said gel has an affinity for ions capable of binding to said gel at said binding sites not occupied by said ionic gelling entity.

47. The method of claim 46, wherein said ionic gelling entity is calcium ions.

48. The method of claim 46, wherein said water-soluble salts of alginic acid and pectic acid are alkali metal salts.

49. The method of claim 48, wherein said alkali metal halts are selected from the group consisting of sodium, potassium and ammonium.

50. The method of claim 46, wherein said step (d) is performed at said pH during a period of time sufficient to lower the content of said ionic gelling entity in the gel between 0.005 times and 0.5 times the ionic gelling entity content corresponding essentially to saturation of the binding sites of the alginate or pectate gel.

51. The method of claim 46, wherein said step (d) is performed at said pH during a period of time sufficient to lower the content of said ionic gelling entity between 0.005 times and 0.05 times the ionic gelling entity content corresponding essentially to saturation of the binding sites of the alginate or pectate gel.

52. A method for preventing or reducing the risk of precipitation of crystals including potassium bitartrate and calcium tartrate in a liquid containing ions capable of forming said crystals, said method comprising contacting said liquid with said alginate or pectate gel partially deficient in ionic gelling entity produced by the method of claim 46 whereby said gel binds said ions capable of forming said crystals at binding sites of said gel not occupied by said ionic gelling entity; and separating said gel having said bound ions capable of forming said crystals.

53. The method of claim 52, wherein said liquid is selected from the group consisting of fruit juice, wine, sparkling wine and champagne.

54. The method of claim 52, wherein said gel is used in a bottle fermentation process for the secondary fermentation of a wine after the addition of sugar to give a sparkling wine.

55. The method of claim 52, wherein said gel contains yeasts.

56. The method of claim 55, wherein the concentration of yeasts ranges between $10^8$ and $6\times10^8$ yeast cells per milliliter of gel.

57. The method of claim 55, wherein said yeasts are selected from the group consisting of *Saccharomyces cerevisiae* and *Saccharomyces bayanus*.

58. The method of claim 55, wherein the quantity of yeast-containing gel which is introduced is about 4 ml to provide a concentration of about $3\times10^8$ yeast cells per milliliter of gel.

59. The method of claim 52, wherein the gel which is partially deficient in calcium ions is used in combination with a calcium alginate gel which is not deficient in calcium ions and includes yeasts.

60. The method of claim 52, wherein said gel is in the form of beads.

* * * * *